United States Patent [19]

Baker

[11] 4,212,941
[45] Jul. 15, 1980

[54] METHOD FOR THE PRODUCTION OF 9-(2-O-ACYL-β-D-ARABINOFURANOSYL-)ADENINE COMPOUNDS

[75] Inventor: David C. Baker, Ann Arbor, Mich.

[73] Assignee: Warner-Lambert Company, Morris Plains, N.J.

[21] Appl. No.: 799,631

[22] Filed: May 23, 1977

Related U.S. Application Data

[62] Division of Ser. No. 687,271, May 17, 1976, Pat. No. 4,055,718.

[51] Int. Cl.$^2$ .................................................. C12P 19/32
[52] U.S. Cl. .................................... 435/92; 435/197; 435/839; 435/896; 435/897; 435/886; 435/872; 435/863; 435/822
[58] Field of Search ..................... 195/28 N; 435/92

[56] References Cited

U.S. PATENT DOCUMENTS

| | | | |
|---|---|---|---|
| 3,304,236 | 2/1967 | Nuesch | 195/29 |
| 3,651,045 | 3/1972 | Haskell et al. | 424/180 |

*Primary Examiner*—Alvin E. Tanenholtz
*Attorney, Agent, or Firm*—Stephen Raines; Albert H. Graddis; Stephen I. Miller

[57] ABSTRACT

9-(2-O-Acyl-β-D-arabinofuranosyl)adenine compounds and their production by enzymatic removal of the 3-O-acyl and 5-O-acyl groups of a 9-(2,3-di-O-acyl-β-D-arabinofuranosyl)adenine compound or a 9-(2,3,5-tri-O-acyl-β-D-arabinofuranosyl)adenine compound. The monoester compounds are useful as antiviral agents. The compounds are water-soluble and lipophilic, thereby being adaptable to a wide variety of pharmaceutical formulations.

5 Claims, No Drawings

METHOD FOR THE PRODUCTION OF 9-(2-O-ACYL-β-D-ARABINOFURANOSYL)ADENINE COMPOUNDS

This is a division of application Ser. No. 687,271, filed May 17, 1976 now U.S. Pat. No. 4,055,718.

SUMMARY AND DETAILED DESCRIPTION

The present invention relates to new organic compounds that are useful as pharmacological agents and to a method for their production. More particularly, the invention relates to new 9-(2-O-acyl-β-D-arabinofuranosyl)-adenine compounds that are represented by the formula

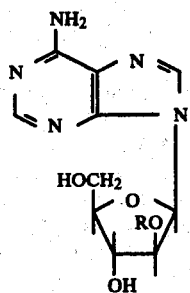

where R is a straight or branched chain alkanoyl group having from 2 to 4 carbon atoms. Examples of alkanoyl groups represented by R are acetyl, propionyl, butyryl, and isobutyryl.

In accordance with the method of the invention, 9-(2-O-acyl-β-D-arabinofuranosyl)adenine compounds having formula I are produced by subjecting to enzymatic removal the 3-O-acyl and 5-O-acyl groups of a 9-(β-D-arabinofuranosyl)-adenine ester compound represented by the formula

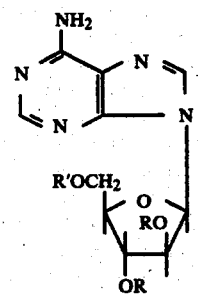

where R has the same significance and R' is hydrogen or a lower alkanoyl group. The method is carried out by contacting the ester compound with the enzyme in an aqueous medium until removal of the 3-O-acyl and 5-O-acyl groups is achieved. The deacylated product having formula I is isolated from the medium by conventional recovery and purification procedures. Enzymes suitable for deacylation are enzymes elaborated by microorganisms of the order Actinomycetales, for example, bacteria of the family Mycobacteriaceae, Streptomycetaceae, Actinomycetaceae, Streptosporangiaceae, and Actinoplanaceae. Also suitable are enzymes elaborated by fungi imperfecti. Especially suitable are strains of *Bacillus subtilis*. *Bacillus subtilis* is preferred as a source of deacylation enzyme because *Bacillus subtilis* is widely available and easy to cultivate. The process also can be carried out with enzymes elaborated by strains of the following exemplary genera and species: Streptomyces (mesophil), such as *S. viridochromogenes, S. fradiae, S. griseus, S. griseoflavus, S. prasinus*; Streptomyces (thermophil), such as *S. violaceoruber, Thermoactinomyces vulgaris, S. thermovulgaris*; Chainia, such as Actinopycnidium species, Micromonospora species, *Nocardia petroleophila, Streptosporangium roseum, Thermopolyspora polyspora, Thermopolyspora glauca, Mycobacterium tuberculosis* var. BCG; *Mycobacterium phlei*; and Cephalosporium and Aspergillus. The preferred acylase, as indicated, is that elaborated by the microorganism *Bacillus subtilis*. The acylase itself need not be isolated but a cell paste, mass or mycelium of the desired microorganism can be used instead.

The aqueous medium for the reaction (or incubation) is maintained at pH 6.5 to 7.5, preferably at pH 7.0 to 7.5. The medium is kept at temperatures ranging from 20° to 45° C., preferably 35° to 40° C., until the desired deacylation is substantially complete, usually 15 to 24 hours. The amount of acylase, or microorganism cell paste or mass used is not critical. Since the rate of deacylation is dependent on the amount of acylase present, it is convenient and preferable to use excess enzyme, e.g., about equal weights of substrate (starting ester) and microorganism cell paste or mass. Following completion of the reaction, the mixture is conveniently freed of solids usually by filtration, and the desired compound is obtained by conventional means, as indicated above.

The 9-(2-O-acyl-β-D-arabinofuranosyl)adenine compounds are new chemical compounds that are useful as pharmacological agents, especially as antiviral agents against herpes virus in oral, topical or parenteral form.

Their activity as antiviral agents can be quantitatively measured in an in vitro test by utilizing the plaque reduction technique first developed by Dulbecco (Proc. Natl. Acad. Sci., Volume 38, pages 747-752) and modified by Hsiung and Melnick (Virology, Volume 1, pages 533-535). In this test, a complete cell monolayer is first grown on a glass test unit. The growth medium is then removed, and the virus is adsorbed on the cell monolayer for a measured time period. In the absence of an antiviral agent, the virus will destroy well-defined areas of cells, called plaques, that can be seen macroscopically when the vital stain, neutral red, is added to the system. To test the inhibiting effect of a given compound, the test compound in solution is added to the virus-cell system, and the whole is covered with a nutrient agar overlay containing neutral red. After incubation, the plaques are counted, and the number of plaques produced in the system containing the test compound is compared with the number produced in the control systems, from which only the test compound is omitted. The inhibitory activity of a test compound is reported as the percentage reduction of the plaque count on the test units compared with that on the controls.

When tested by this plaque reduction technique, with 4 oz. glass bottles serving as the test units and H. Ep. No. 2 cells making up the cell monolayer, compounds of the invention, at a concentration of about 15 to 60 micrograms/ml. in Hank's Balanced Salt Solution (pH 7-8), typically were found to give substantially complete plaque reduction against herpes simplex.

The ester compounds of the invention structurally resemble 9-(β-D-arabinofuranosyl)adenine, which is known to be an antiviral agent that is active against herpes virus. The latter compound has been reported to be more active in vitro against herpes virus than its 5'-benzoyl ester whereas its 5'-palmitate ester was inactive in the same test (Renis et al., J. Med. Chem., 16, 754); the compound has also been reported (Repta et al., J. Pharm. Sci., 64, 392) to be poorly soluble in water (and subject to enzymatic deamination in the corresponding biologically inactive hypoxanthine) and its 5'-formate ester, relatively water-soluble, to be unstable in aqueous solution. Other relatively poorly water-soluble esters of 9-(β-D-arabinofuranosyl)adenine are the triesters described in U.S. Pat. No. 3,651,045. It is therefore surprising that the compounds of the invention, unlike the prior art compounds, exhibit good antiviral activity, are resistant to enzymatic deamination, and are adaptable to aqueous and non-aqueous pharmaceutical formulation, being readily soluble in water and/or being lipophilic. Preferred compounds of the invention in this regard are 9-(2-O-acetyl-β-D-arabinofuranosyl)adenine and 9-(2-O-propionyl-β-D-arabinofuranosyl)adenine.

The invention is illustrated by the following examples.

EXAMPLE 1

To a stirred suspension of 500 mg. of 9-(2,3,5-tri-O-acetyl-β-D-arabinofuranosyl)adenine (U.S. Pat. No. 3,651,045, supra) in 50 ml. of a 0.1 M pH 7 phosphate buffer is added 500 mg. of Bacillus subtilis ATCC 6633 cell paste or lyophilizate (U.S. Pat. No. 3,304,236, Example 9) and the mixture is stirred for 22 hours at 35°–40° C., with periodic addition of saturated aqueous sodium bicarbonate to maintain the pH at 7.0 to 7.5. The incubated mixture is then poured into 150 ml. of methanol and the resulting mixture is filtered through diatomaceous earth and the filtrate evaporated at reduced pressure. The residue is passed through a $1 \times 30$ cm. column of dry silica gel, and the column is eluted sequentially with 5:95, 10:90 and 20:90 (v/w) methanol-chloroform. The eluate is collected in 10-ml. fractions and those that contain the desired product, as established by thin layer chromatography, are combined and evaporated at reduced pressure to give the desired product 9-(2-O-acetyl-β-D-arabinofuranosyl)adenine; $\lambda_{max}^{CH3OH} = 259$ nm. The structure is confirmed by nmr spectra.

By substituting 500 mg. of 9-(2,3-di-O-acetyl-β-D-arabinofuranosyl)adenine for the 9-(2,3,5-tri-O-acetyl-β-D-arabinofuranosyl)adenine in the above procedure, the same end product is obtained.

EXAMPLE 2

By substituting 500 mg. of either 9-(2,3,5-tri-O-propionyl-β-D-arabinofuranosyl)adenine or 9-(2,3-di-O-propionyl-β-D-arabinofuranosyl)adenine for the 9-(2,3,5-tri-O-acetyl-β-D-arabinofuranosyl)adenine in Example 1, the product obtained is 9-(2-O-propionyl-β-D-arabinofuranosyl)-adenine; m.p. 206.5°–207.5° C. after crystallization from ethanol, $\lambda_{max}^{CH3OH} = 259$ nm ($\epsilon = 14{,}600$), partition coefficient, 1.55 (pentanol/water).

EXAMPLE 3

By substituting 500 mg. of either 9-(2,3,5-tri-O-isobutyryl-β-D-arabinofuranosyl)adenine or 9-(2,3-di-O-isobutyryl-β-D-arabinofuranosyl)adenine for the 9-(2,3,5-tri-O-acetyl-β-D-arabinofuranosyl)adenine in Example 1, the product obtained is 9-(2-O-isobutyryl-β-D-arabinofuranosyl)adenine.

Preparation of Diacyl Ester Starting Materials

The 9-(2,3-di-O-acyl-β-D-arabinofuranosyl)-adenine starting materials specified above are new compounds. These compounds can be prepared from known materials by the following procedure.

(a) To a well-stirred suspension of 26.7 g. of 9-β-D-arabinofuranosyladenine in 500 ml. of dry dimethylformamide, containing 16.3 g. of imidazole, is added 18.1 g. of tert-butylchlorodimethylsilane. The mixture is stirred, with protection from moisture, for 20 hours at room temperature, then evaporated at reduced pressure at 50°–60° C. The residue is dissolved in 300 ml. of ethyl acetate and the solution is washed with water, dried and evaporated at reduced pressure. The residual syrup is dissolved in 240 ml. of hot chloroform; the solution is diluted to cloudiness with hexane and cooled to crystalline 9-[5-O-(tert-butyldimethysilyl)-β-D-arabinofuranosyl]adenine, which is collected by filtration, washed with hexane and dried at 80° C. at reduced pressure; m.p. 157°–158° C., $[\alpha]_D^{23} = +4.1°$, $\lambda_{max}^{CH3OH} = 259$ nm ($\epsilon = 15{,}000$).

(b) To a well-stirred solution of 15.4 g. of 9-[5-O-(tert-butyldimethylsilyl)-β-D-arabinofuranosyl]-adenine in 200 ml. of dry pyridine is added 9.44 ml. of acetic anhydride. The solution is stirred at room temperature for 16 hours, treated with 100 g. of chipped ice and stirred one additional hour. The resulting solution is evaporated at reduced pressure at 45° C. and the residue is dissolved in 250 ml. of chloroform. The chloroform solution is washed with aqueous sodium bicarbonate and with water, and is dried and evaporated. The residual product, 9-[2,3-di-O-acetyl-5-O-(tert-butyldimethylsilyl)-β-D-arabinofuranosyl]adenine, is suitable for use as a starting material for the procedure of paragraph (c) without further purification.

(c) The product of (b) is dissolved in 300 ml. of tetrahydrofuran, the solution is treated with 2.3 ml. of glacial acetic acid and 31.3 g. of tetrabutylammonium fluoride and allowed to stand at room temperature for 2 hours. The solution is then passed over a $5 \times 10$ cm. column of dry silica gel. The column is eluted with one liter of tetrahydrofuran and the eluate is evaporated at reduced pressure to give the product 9-(2,3-di-O-acetyl-β-D-arabinofuranosyl)adenine; m.p. 138°–139° C. after crystallization from acetone, $[\alpha]_D^{23} = -4.1°$ (c=1% in methanol), $\lambda_{max}^{CH3OH} = 259$ nm ($\epsilon = 15{,}000$).

(d) From 15.0 g of 9-[5-O-(tert-butyldimethylsilyl)-β-D-arabinofuranosyl]adenine and 11.1 ml. of propionic anhydride in 100 ml. of dry pyridine, following the procedure of (b), there is obtained 9-[5-O-(tert-butyldimethylsilyl)-2,3-di-O-propionyl-β-D-arabinofuranosyl]adenine, which, on reaction with 31.3 g. of tetrabutylammonium fluoride in 200 ml. of tetrahydrofuran and 2.3 ml. of glacial acetic acid, following the procedure of (c), gives 9-(2,3-di-O-propionyl-β-D-arabinofuranosyl)adenine; m.p. 172°–173° C. after crystallization from acetone, $[\alpha]_D^{23} = -4.1°$ (c=1% in methanol), $\lambda_{max}^{CH3OH} = 259$ nm ($\epsilon = 15{,}000$). From 1.79 g. of 9-[5-O-(tert-butyldimethylsilyl)-β-D-arabinofuranosyl]adenine and 2.34 ml. of isobutyryl chloride in 50 ml. of dry pyridine, following the procedure of (b), there is obtained 9-[5-O-tert-butyldimethylsilyl)-2,3-di-O-isobutyryl-β-D-arabinofuranosyl]adenine, which, on reaction with 3.7 g. of tetrabutylammonium fluoride in 100 ml. of tetrahydrofuran and 0.5 ml. of glacial acetic acid, following the procedure of c), gives 9-(2,3-di-O-isobutyryl-β-D-arabinofuranosyl)adenine; m.p. 207°-208° C. after crystallization from acetone, $\lambda_{max}^{CH3OH}=259$ nm ($\epsilon=15,000$).

I claim:

1. A method for the production of a 9-(2-O-acyl-beta-D-arabinofuranosyl)adenine compound having the formula

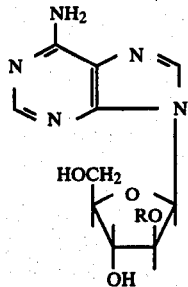

I wherein R is a straight or branched chain alkanoyl group having from 2 to 4 carbon atoms which comprises contacting a 9-(beta-D-arabinofuranosyl)adenine ester compound represented by the formula

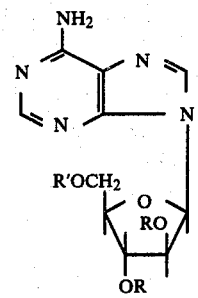

II where R has the same significance and R' is hydrogen or a lower alkanoyl group with an acylase capable of deacylating the 3 and 5-O-acyl groups; said contacting being carried out at 20°-45° C. at a pH of 6.5-7.5, and recovering the product.

2. Method according to claim 1 where the acyl removal is carried out at temperatures ranging from 35° to 40° C. in an aqueous medium at pH 7 to 7.5 using approximately equal weights of the ester compound and enzyme elaborating microorganism cell mass.

3. Method according to claim 2 where the enzyme elaborating microorganism is a strain of *Bacillus subtilis*.

4. Method according to claim 1 where the ester compound is a 2-O-acetyl ester compound.

5. Method according to claim 1 where the ester compound is a 2-O-propionyl ester compound.

* * * * *